United States Patent [19]
Brown et al.

[11] Patent Number: 5,131,816
[45] Date of Patent: Jul. 21, 1992

[54] CARTRIDGE FED PROGRAMMABLE AMBULATORY INFUSION PUMPS POWERED BY DC ELECTRIC MOTORS

[75] Inventors: Eric W. Brown, Newport Beach; Charles M. Kienholz, San Dimas; Steven J. Busak, Laguna Niguel; Wayne Hayob, Mission Viejo; Ferrell D. Papic, Orange, all of Calif.

[73] Assignee: I-Flow Corporation, Irvine, Calif.

[21] Appl. No.: 351,981

[22] Filed: May 15, 1989

Related U.S. Application Data

[63] Continuation-in-part of Ser. No. 216,512, Jul. 8, 1988, Pat. No. 4,950,245, and Ser. No. 301,628, Jan. 24, 1989, Pat. No. 5,011,378.

[51] Int. Cl.⁵ ............................................. F04B 41/06
[52] U.S. Cl. ......................................... 417/2; 417/12; 417/18; 417/45; 417/234; 417/474; 417/478; 604/65; 604/153; 128/DIG. 12
[58] Field of Search ................ 417/2, 12, 15, 18, 44, 417/45, 234, 474, 478; 604/65, 153; 128/DIG. 12, DIG. 13

[56] References Cited

U.S. PATENT DOCUMENTS

| | | |
|---|---|---|
| 2,351,828 | 8/1944 | Marsh . |
| 2,412,397 | 12/1946 | Harper . |
| 3,391,600 | 7/1968 | Archibald . |
| 3,778,195 | 12/1973 | Bamberg . |
| 4,094,318 | 6/1978 | Burke et al. . |
| 4,142,524 | 3/1979 | Jassawalla et al. . |
| 4,199,307 | 4/1980 | Jassawalla . |
| 4,273,121 | 6/1981 | Jassawalla . |
| 4,340,153 | 7/1982 | Spivey . |
| 4,397,639 | 8/1983 | Eschweiler et al. . |
| 4,479,761 | 10/1984 | Bilstad et al. . |
| 4,479,797 | 10/1984 | Kobayashi et al. . |
| 4,493,704 | 1/1985 | Beard et al. . |
| 4,493,706 | 1/1985 | Borsanyi et al. ............. 604/153 |
| 4,498,843 | 2/1985 | Schneider et al. . |
| 4,559,038 | 12/1985 | Berg et al. ................... 604/153 |
| 4,563,175 | 1/1986 | LaFond . |
| 4,601,700 | 7/1986 | Thompson et al. . |
| 4,650,469 | 3/1987 | Berg et al. . |
| 4,653,987 | 3/1987 | Tsuji et al. . |
| 4,657,486 | 4/1987 | Stempfle et al. . |
| 4,657,490 | 4/1987 | Abbott . |
| 4,666,430 | 5/1987 | Brown et al. . |
| 4,673,390 | 6/1987 | Archibald . |
| 4,696,671 | 9/1987 | Epstein et al. . |
| 4,705,506 | 11/1987 | Archibald . |
| 4,718,467 | 1/1988 | Di Gianfilippo et al. . |
| 4,725,205 | 2/1988 | Cannon et al. . |
| 4,728,265 | 3/1988 | Cannon . |
| 4,731,057 | 3/1988 | Tanaka et al. . |
| 4,734,092 | 3/1988 | Millerd . |
| 4,741,732 | 5/1988 | Crankshaw et al. .......... 604/50 |
| 4,741,736 | 5/1988 | Brown . |
| 4,756,706 | 7/1988 | Kerns et al. . |
| 4,781,548 | 11/1988 | Alderson et al. . |
| 4,808,078 | 2/1989 | Havens et al. ................ 417/45 |
| 4,865,584 | 9/1989 | Epstein et al. . |
| 4,890,984 | 1/1990 | Alderson et al. . |
| 4,908,017 | 3/1990 | Howson et al. ......... 128/DIG. 12 |
| 4,925,371 | 5/1990 | Griesmar ..................... 417/18 |
| 4,950,245 | 8/1990 | Brown et al. . |

FOREIGN PATENT DOCUMENTS

| | | |
|---|---|---|
| WO8101728 | 6/1981 | European Pat. Off. . |
| 0204977 | 12/1986 | European Pat. Off. . |
| WO8911302 | 11/1989 | European Pat. Off. . |
| 2855713 | 6/1980 | Fed. Rep. of Germany . |
| 3500467 | 7/1986 | Fed. Rep. of Germany . |

Primary Examiner—Richard A. Bertsch
Assistant Examiner—David W. Scheuermann
Attorney, Agent, or Firm—Robert M. Asher

[57] ABSTRACT

A cartridge fed infusion pump containing a plurality of linear peristaltic pumps. Each pump is powered by a direct current motor. The motor has a shaft which rotates to perform a pump cycle. A position encoder mounted on the shaft is used to determine when the shaft has reached the stop position in the pump cycle. A reverse pulse is used to quickly stop the motor shaft.

33 Claims, 12 Drawing Sheets

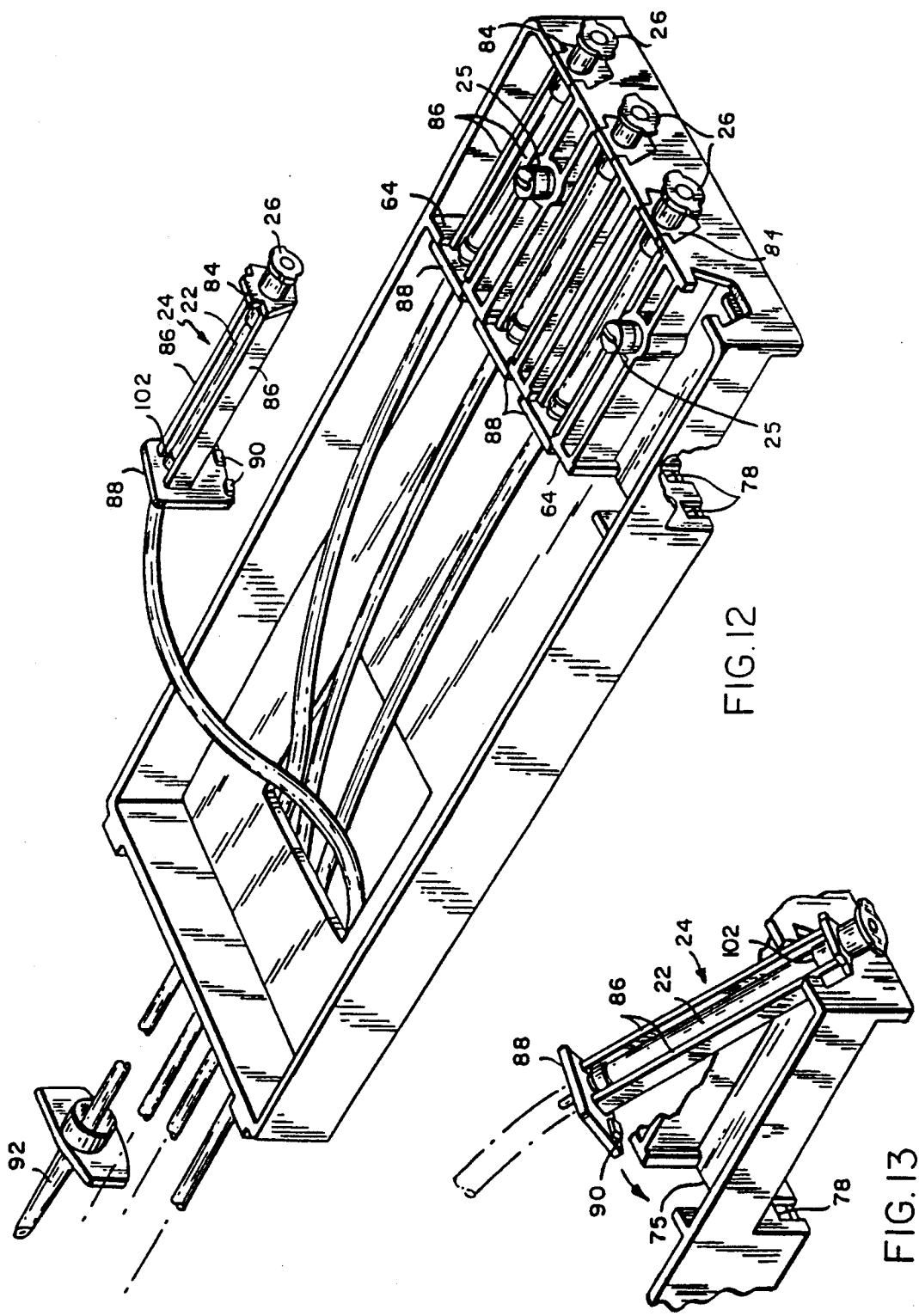

CARTRIDGE FED PROGRAMMABLE AMBULATORY INFUSION PUMPS POWERED BY DC ELECTRIC MOTORS

This is a continuation-in-part of U.S. Pat. application Ser. No. 07/216,512, filed Jul. 8, 1988, now issued as U.S. Pat. No. 4,950,245 and U.S. Pat. application Ser. No. 07/301,628, filed Jan. 24, 1989, now issued as U.S. Pat. No. 5,011,378.

BACKGROUND OF THE INVENTION

This invention relates to a programmable cartridge fed ambulatory infusion pump powered by a DC electric motor.

It is an object of this invention to provide a compact, lightweight infusion pump which may be used for ambulatory patients. It is a further object of this invention to provide a pump which can be conveniently used with fluid source cartridges.

There has been a demonstrated need for pumps which can intravenously administer a plurality of drug solutions. For example, multiple drug chemotherapy treatments have been used to treat diseases such as cancer. Many of the drugs used in chemotherapy and other therapies cannot be mixed together prior to an infusion. Some of these drugs react to neutralize one another. Other drugs react to form precipitates which may block the catheter tube or possibly cause an embolism in the patient. Pumps have been developed which can concurrently pump a plurality of fluids through a multilumen catheter into a patient. The multilumen catheter keeps the drugs separate until they reach the bloodstream. For example, in U.S. Pat. No. 4,741,736 (Brown), a pump is disclosed which uses a roller to push fluid out of a plurality of compartments in an infusion pump. The different fluids in each of the compartments are pumped out at the same time by the action of the single roller.

In infusion pump patent, U.S. Pat. No. 4,666,430 (Brown and Tai), a multiple syringe pump is disclosed in which a canister of compressed gas serves as the power source for pumping fluid out of a syringe. All of the syringes are controlled by the same canister of gas and variation in the pumping rate of a syringe is controlled by valves on the outlets of the syringes.

It is an object of the present invention to provide in a single ambulatory housing, separately and accurately controlled pumping mechanisms for each of a plurality of fluid sources. It is typical in infusion pumps where accurate infusion rates are desired to use a stepper motor. However, in providing an ambulatory pump, it is desirable to use smaller, lighter motors such as the dc electric motors of the present invention. A further object of the present invention is to provide controlled infusion rates with dc electric motors.

In order to deliver fluid at a precisely determined rate through a linear peristaltic pump, the pump value must be accurately positioned with respect to the fluid delivery tube. Any warping of the cartridge or any mispositioning of the pump may permit a leak when a pump valve is depressed against the tube. It is an object of this invention to provide a cartridge and tube mount which accurately position a tube within an infusion pump. It is desirable that accuracy be obtained using low cost plastic pieces.

SUMMARY OF THE INVENTION

The present invention is directed to an infusion pump system including a fluid source cartridge which is attachable to a pump housing. The pump housing has a plurality of linear peristaltic pumps. Fluids may be stored in the cartridge or provided through the cartridge from an external source such as an IV bag mounted on a pole. The cartridge has a linear fluid conduit which aligns with the peristaltic pump for each fluid when the cartridge is inserted into the housing. The conduits are provided in what is called herein the pump interface portion of the cartridge. The pumping of fluid through any of the fluid conduits in the cartridge is controlled by that conduit's respective peristaltic pump.

The infusion pump housing may be advantageously provided with a programmable controller to permit individual control over each of the peristaltic pumps. This permits operating the pump sequentially or concurrently and at any selected pumping rate.

The pump according to the present invention is operated by a direct current motor. A position encoder rotatable in conjunction with the shaft of the motor provides an indication of a full cycle of the motor. Thus, by controlling the time delay between each motor cycle, the infusion pump rate can be controlled. The motor can be operated in reverse to assist it in stopping at the stop position indicated by the position encoder.

To provide accurate positioning of fluid pump tube with respect to the infusion pump, the cartridge of the present invention is provided with a handle clamp. The clamp is located in the pump interface portion of the cartridge. The clamp includes a bar which gives support to the pump interface portion, thereby holding the pump tubes firmly in position against the infusion pump.

Other objects and advantages of the present invention will become apparent during the following description of the presently preferred embodiment of the invention taken in conjunction with the drawings.

DETAILED DESCRIPTION OF THE DRAWINGS

FIG. 12 is an isometric view of a cartridge of the present invention for use with pole mounted fluid source pouches along with pump tube mounts.

FIG. 13 illustrates how a pump tube mount is inserted into the cartridge.

DETAILED DESCRIPTION OF THE PREFERRED EMBODIMENTS

Figure 1:
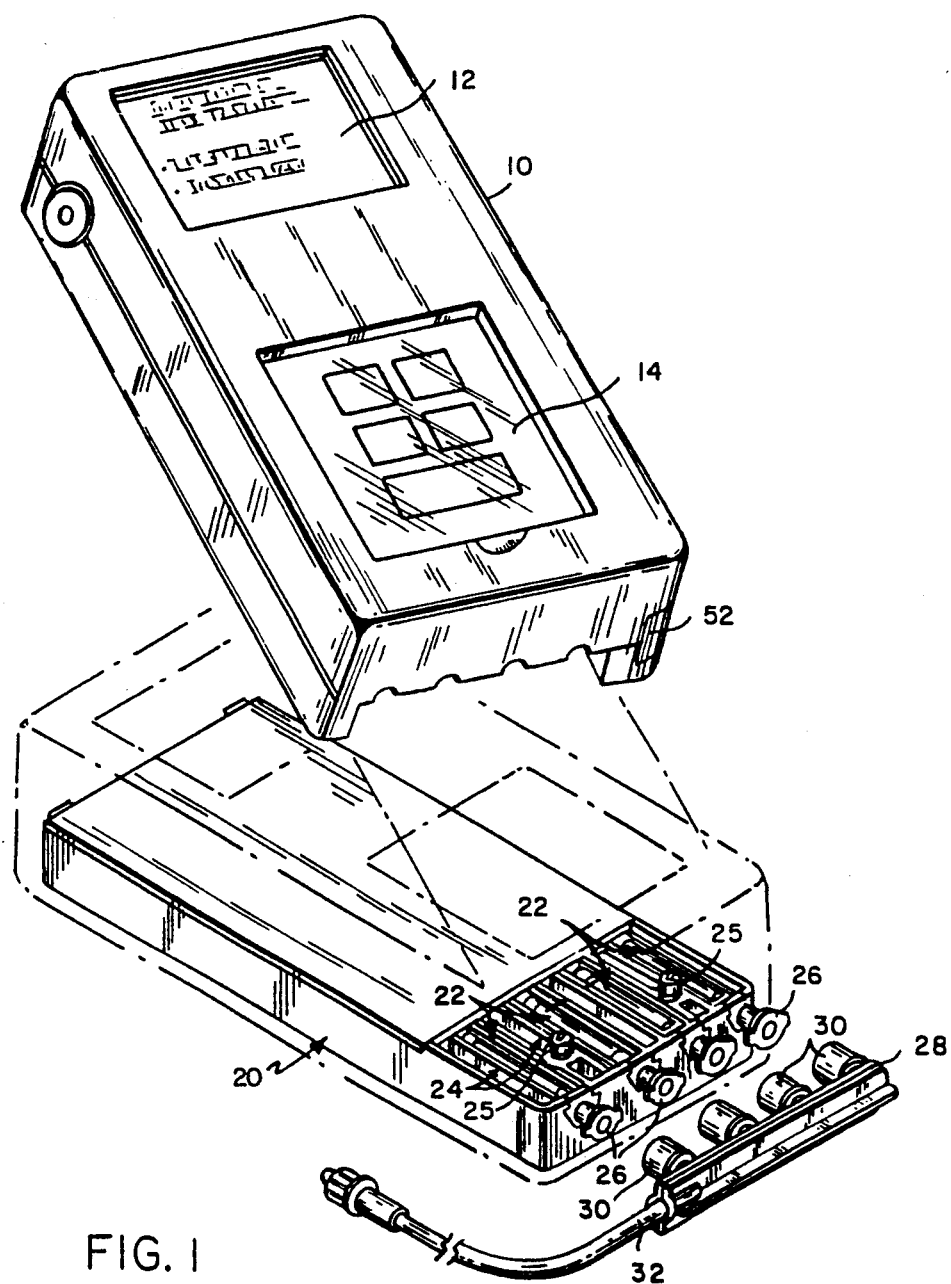
FIG. 1 is an isometric view of a pump and a cartridge of the present invention.
Figure 2:
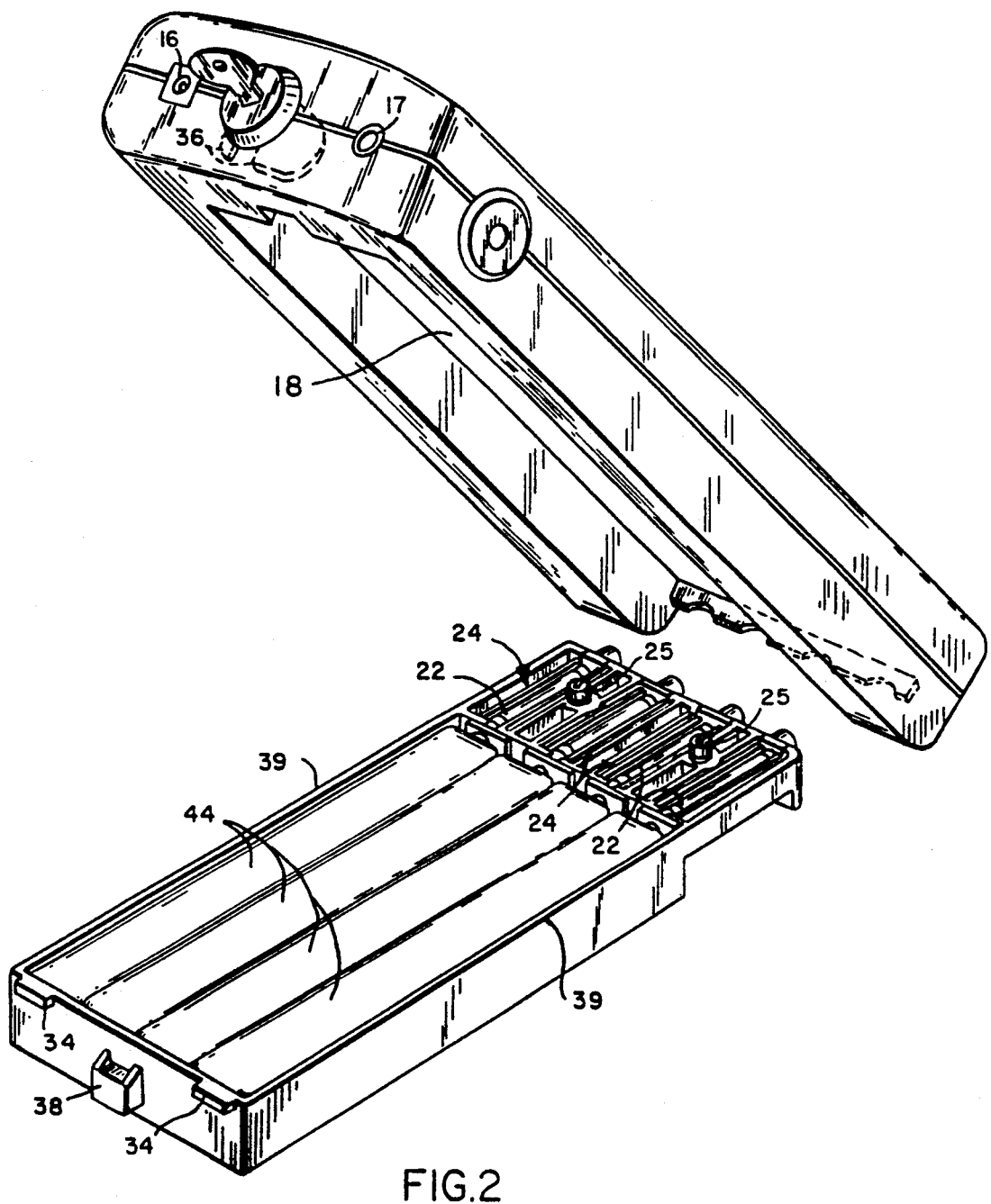
FIG. 2 is a second isometric view of the cartridge and pump of the present invention.

Referring now to FIG. 1, a pump housing 10 is provided for pumping fluid from a multiple fluid cartridge 20. The pump housing 10 is provided with a liquid crystal display 12, a keyboard 14 and as shown in FIG. 2, programming jack 16. The underside of the pump housing 10 forms a cavity for receiving the cartridge 20. The cavity extends through one end of the pump housing 10.

The cartridge 20 houses one or more pump tube mounts 24. The portion of the cartridge 20 housing the pump tube mounts 24 is referred to herein as the pump interface portion. The remainder of the cartridge is referred to as the fluid source portion. Each pump tube mount 24 is connected to a fluid source which is either stored in a bag or a pouch in the fluid source portion of the cartridge or stored on a bag hanging from an intravenous delivery pole. To connect with a bag hanging from a pole, the cartridge's fluid source portion may have a window through which tubing may be inserted to connect the bag with the tube mount. Each pump tube mount 24 includes a compressible tube 22 made from a material which is inert to the fluids which will be fed through the tube. At the outer end of the pump tube mount 24, a luer connector 26 serves as the outlet for delivering fluid into an output lumen.

Individual output lumens may be connected to each of the luer connectors 26. These lumens may remain separate or they may be fused together to form a multilumen tube for outputting the fluid to a connector for making connection with an implanted catheter, for example. The multilumen output tube may be connected to any of a variety of multilumen connectors. A needle connector may be used in which each lumen is connected to a hollow injection needle. The needle connector may be inserted through a silicone block to make connection with a connector for a multilumen catheter. Another option is a multilumen connector such as that described in co-pending U.S. Pat. application Ser. No. 07/178,673 filed on Apr. 7, 1988, now issued as U.S. Pat. No. 4,950,255 owned by the same assignee as the present invention. The disclosure of said application is hereby incorporated by reference herein. A third possibility for the multilumen output tube is to connect each lumen separately to a luer connector so that individual connections can be made to four separate catheter lines.

An alternative connector for delivering fluid from the cartridge to a patient may be a single lumen manifold 28 as shown in FIG. 1. The manifold 28 can be provided with four connectors 30 for securely attaching to the luer connectors 26, extending from the cartridge. Each of these connections may then lead to a single lumen 32. When this type of connector is used, it is normal practice to make the fluid source furthest from the manifold output a flushing solution. With this arrangement, the pump generally delivers one solution at a time or one fluid in conjunction with the flushing solution. Before switching from one solution to another, the flushing solution is delivered to clean out the single lumen so as to prevent intermixing of different fluid solutions. This would be necessary in the case of drugs which are either incompatible or which cause precipitation when mixed.

The cartridge 20 is provided with several positioning tabs 34 which extend from the rear end of the cartridge. The tabs 34 are inserted into holes located in the rear of the cavity of the pump. The engagement of the tabs 34 with the holes secures one end of the cartridge in the pump 10. The other end is secured by clamp heads 25 whose operation will be discussed in greater detail with respect to FIGS. 8-11.

The cartridge 20 may be used with a pump having a key operated latch 36. The latch 36 engages a tab 38 extending from the rear end of the cartridge 20. The latch 36 is used as a lock to prevent tampering with the drug solutions stored within the cartridge.

FIG. 2 illustrates flexible pouches 44 used as the fluid sources within the cartridge 20. Each fluid source pouch 44 is connected to a pump tube mount 24. At present, the following procedure is suggested for using the cartridge 20 when it is provided with empty pouches 44. The desired fluid is injected into the connector outlet 26, using a syringe or other conventional means. After filling the pouch 44 with the desired amount of fluid, the connector outlet 26 is attached to the output line. When all of the pouches are filled with their fluid, the cartridge may be inserted into the pump housing 10 and a purge cycle may be run on each of the fluid sources to pump out all of the air which may have gotten into the pouch or pump tube. After purging the air, the cartridge 20 is ready for use in an infusion.

Figure 3:
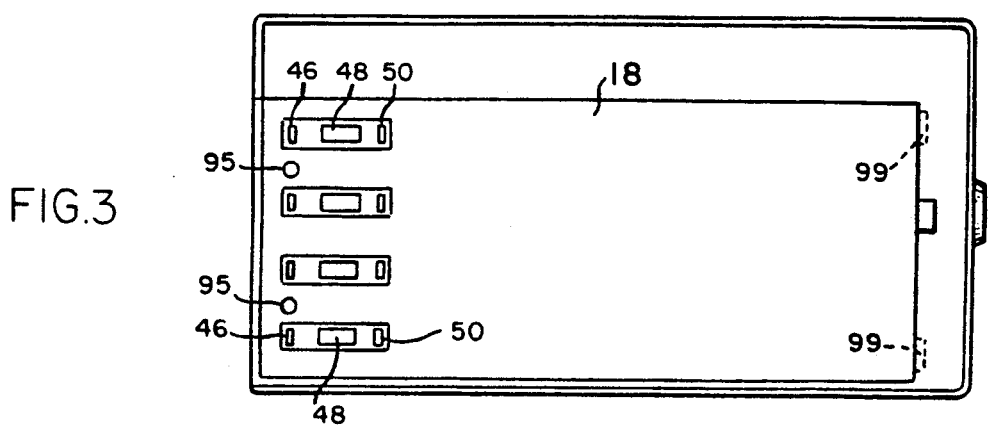
FIG. 3 is a bottom plan view of a pump of the present invention without the cartridge in place.
Figure 4:
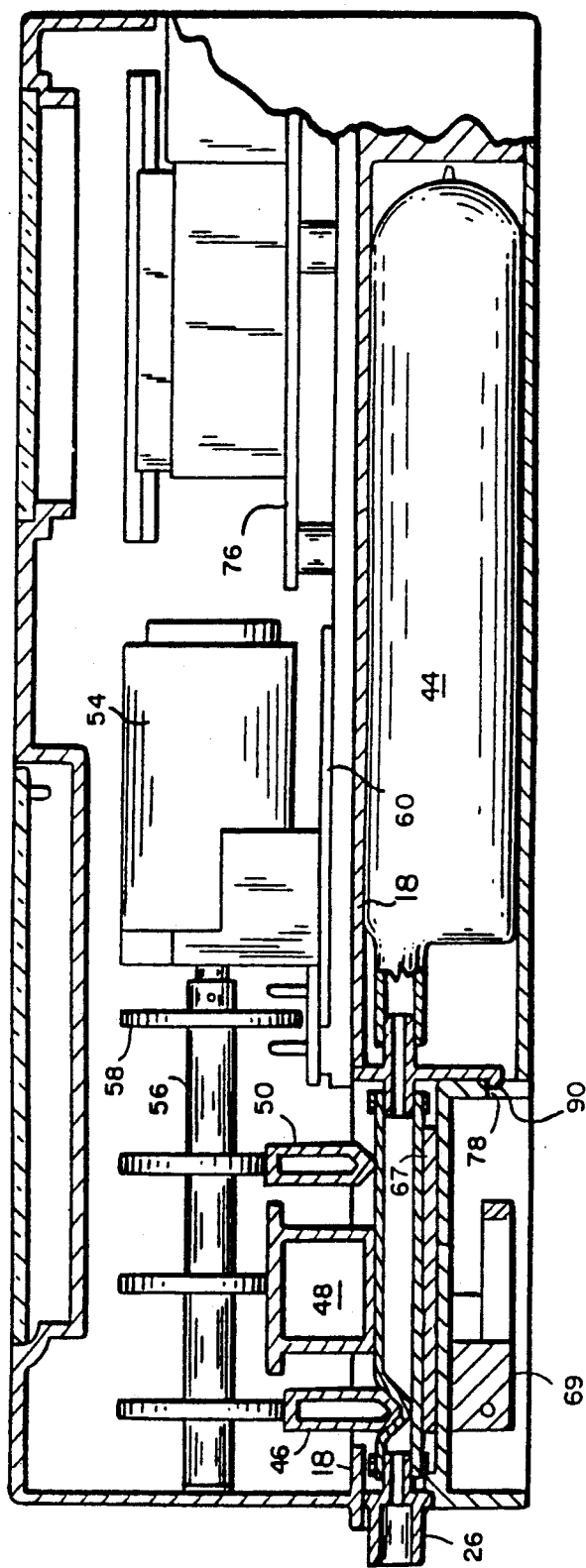
FIG. 4 is a side cross-sectional view of a pump and the cartridge of the present invention.
Figure 4A:
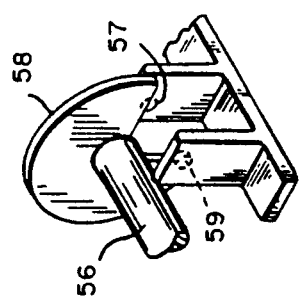
FIG. 4A is a close-up view of the optical sensor and position encoder of the pump of FIG. 4.

Referring now to FIGS. 3 and 4, the presently preferred pump for use with the present invention is provided with a plurality, four in this case, of linear peristaltic pumps. The illustrated pump is a three finger pump, called such because of the three cams which are repeatedly lowered and raised to provide the desired pumping action. Each pump rotates a cam shaft 56 which selectively pushes against three cam followers or "fingers", including an output valve 46, a pump plunger 48 and an input valve 50. Power for the pump may be provided by a battery pack which can be loaded into a cavity behind a battery cover 52 alongside the peristaltic pumps within the housing 10. Alternatively, power can be provided through a jack 17. Each pump is provided with its own motor 54 which turns a cam shaft 56. In accordance with the present invention, each motor 54 is a direct current electric motor. The cam shaft 56 is provided with a timing disk or position encoder 58 shown in greater detail in FIG. 4A. The timing disk is solid except for a sector which is removed. The disk can thus be read by an optical sensor circuit 152 on a printed circuit board 60 to count the rotations, thereby controlling the rate and location of the cam shaft 56. The optical sensor includes a light emitting diode 57 and a photodetector 59.

To maintain improved accuracy, the cam followers should be made to always press against the tube 22, even when in the open position. The pump tube 22 is supported relative to the cam followers by a rigid base 67. A clamp, including clamp handle 69 and clamp heads 25, ensures that the rigid base 67 is always positioned a fixed distance from the cam followers on the pump.

Pumping is performed as follows. With the pump plunger 48 and the input valve 50 retracted, the output valve 46 is lowered to close off the fluid conduits. This permits the pump tube 22 to fill with fluid. This is the preferred position whenever the pump is inactive. In this position, the open sector of the position encoder is aligned with the light emitting diode and photo receiver. Next, the input valve 50 is lowered to close off the pump tube 22 and prevent fluid from flowing back into the fluid source 44. The cam shaft is then turned permitting the tube 22 to expand, pushing the output valve 46 to open. The pump plunger 48 is activated by the cam shaft to push fluid out of the tube 22 and through the outlet 26. Then the output valve 46 is again closed. The pump plunger 48 and the input valve 50 are permitted to open, thereby allowing the pump tube to refill with fluid. Thus, fluid is pumped out of the fluid source. The pump tube in the presently preferred embodiment has an inner diameter of 0.086 inches, an outer diameter of 0.156 inches and a 50 durometer Shore A. The rate of pumping is controlled by knowing the precise volume pumped in each cycle and monitoring the number of pumping cycles per unit of time. The presently preferred embodiment pumps 50 microliters in each pump cycle.

A programmable microprocessor is provided on a control circuit board 76. Each of the four pump motors is controlled by the motor control board 60 and the controller board 76. The control circuits are described in greater detail below with respect to FIGS. 18 and 19. Since each fluid source has its own pump and pump motor, the rate and sequence of fluid infusion is entirely flexible. With a sufficient power source, infusions may take place concurrently or sequentially and at any rate. The present embodiment can pump fluid anywhere between 0.01 and 200 milliliters per hour. The desired sequence and rates of infusion are programmed into the controller board 76 through the programming jack 16. Thus, in accordance with the present pump, multiple fluid infusion treatments may be delivered to a patient in any number of sequences and rates. Thus, the pump provides physicians with great latitude for selecting multiple-fluid drug regimens for treating patient illnesses.

Figure 5:
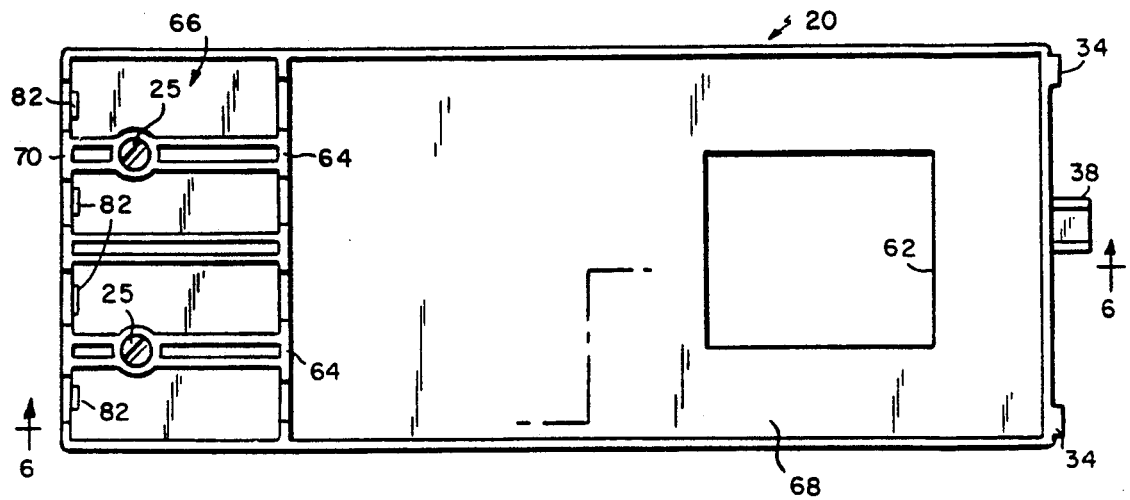
FIG. 5 is a plan view of a cartridge for use in the present invention.
Figure 6:
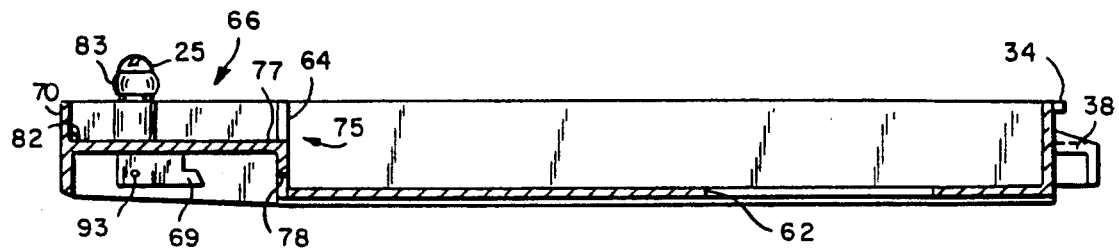
FIG. 6 is a side elevational view of the cartridge of FIG. 6.
Figure 7:
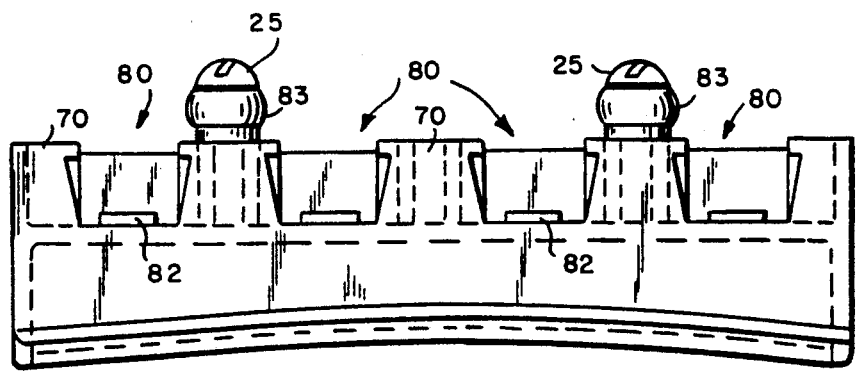
FIG. 7 is an elevational view of the cartridge of FIG. 5
Figure 17:
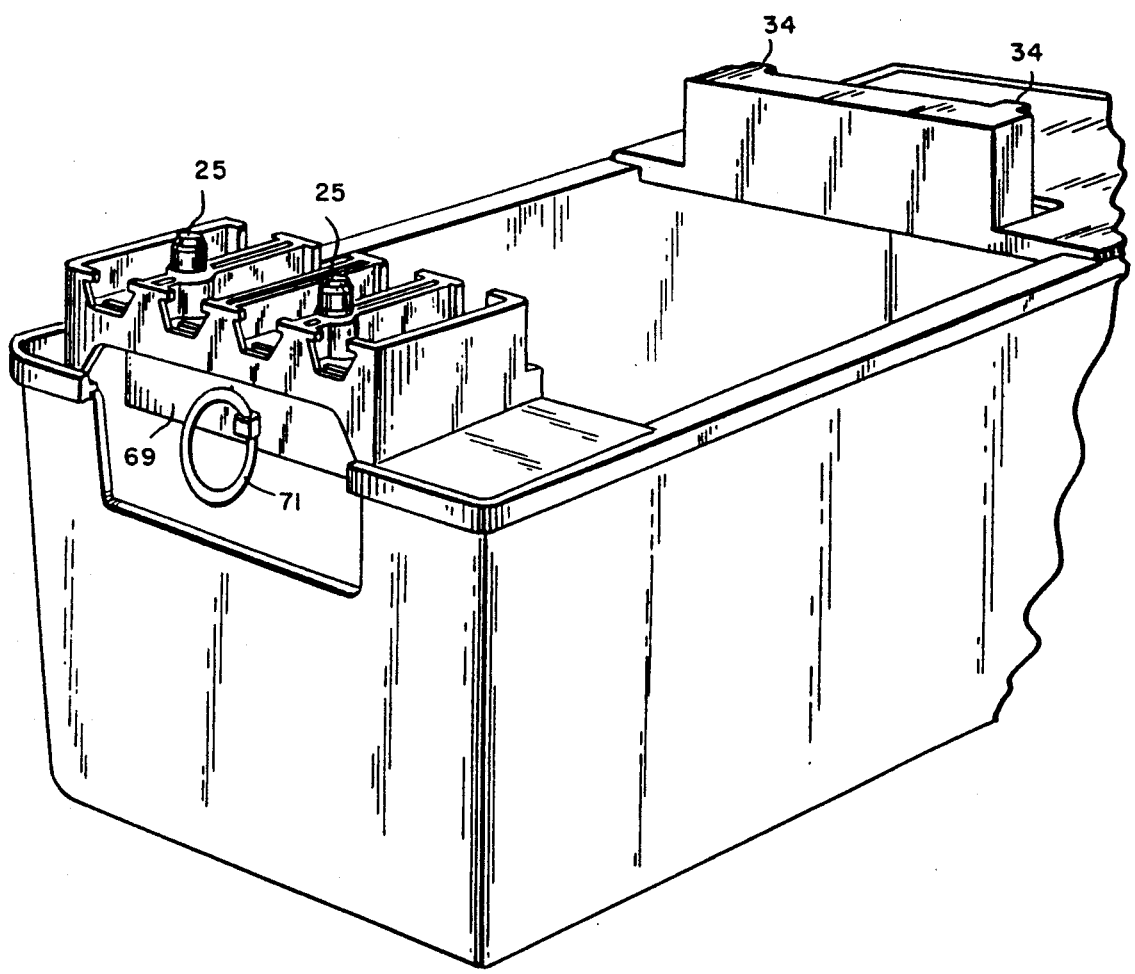
FIG. 17 is an isometric view of a cartridge of the present invention for use with mini-bag fluid sources.

Referring now to FIGS. 5-7, the cartridge 20 shall be described in greater detail. The cartridge of the presently preferred embodiment is made of polycarbonate. FIG. 5, illustrates a cartridge 20 of the type with a window 62. The window provides a hole through which tubing can be fed to connect the pump tubes 22 with fluid sources. A discontinuous dividing wall 64 separates the cartridge 20 into a pump interface portion 66 and a fluid source portion 68. The fluid source portion 68 may provide fluids through a window such as that shown in FIG. 5. Alternatively, the fluid source portion 68 may be filled with fluid source pouches 44. With the pouches 44, the cartridge 20 can be used by an ambulatory patient. The cartridge 20 with a window 62 permits the same pump apparatus to be used with a pole mounted infuser and IV bags. Alternatively, the fluid source portion 68 of the cartridge 20 can be made extra deep, as shown in FIG. 17, to provide room for drug solution mini-bags. Such mini-bags provide more volume of fluid than the pouches 44. The mini-bag cartridge of FIG. 17 includes an inclined floor to help urge the fluid in the mini-bags towards the opening in the bottom of the bag. As such, the pump apparatus can be used with the mini-bags to provide a portable infusion apparatus which can be used by a patient undergoing high fluid volume infusions in the home. The mini-bag cartidge is provided with an opening for access to its clamp handle. A ring 71 may be attached to the handle for easier operation in pulling the handle open.

Referring to FIG. 6, a ledge 75 is formed by the dividing wall 64. The ledge 75 has an upper edge 77 at the level of the base of the pump interface portion of the cartridge. The ledge 75 has a lower edge 78 or a series of individual lower edges 78 which are provided for engaging the pump tube mounts.

The end wall 70 of the cartridge has a series of uniquely shaped openings 80 which accommodate the outlet ends of the pump tube mounts. Immediately behind each opening 80 is a retaining stump 82. The opening 80 is shaped to secure the front wall 84 of the pump tube mount in two directions. The front wall 84 is prevented from moving up and down or left and right when installed within the cartridge opening 80. Furthermore, the opening 80 is given a unique shape as if it were a lock for a key. Just as a key may be uniquely designed to fit into a lock, the front wall 84 of a pump tube mount can be uniquely shaped to fit the unique shape of the opening 80. This feature helps to ensure that only the appropriate tube mounts are inserted into the cartridge. The retaining stump 82 prevents the wall from moving back into the cartridge. The final direction of freedom is secured by the interaction of the rear wall of the pump mount with the ledge 75 of the cartridge.

Figure 8:
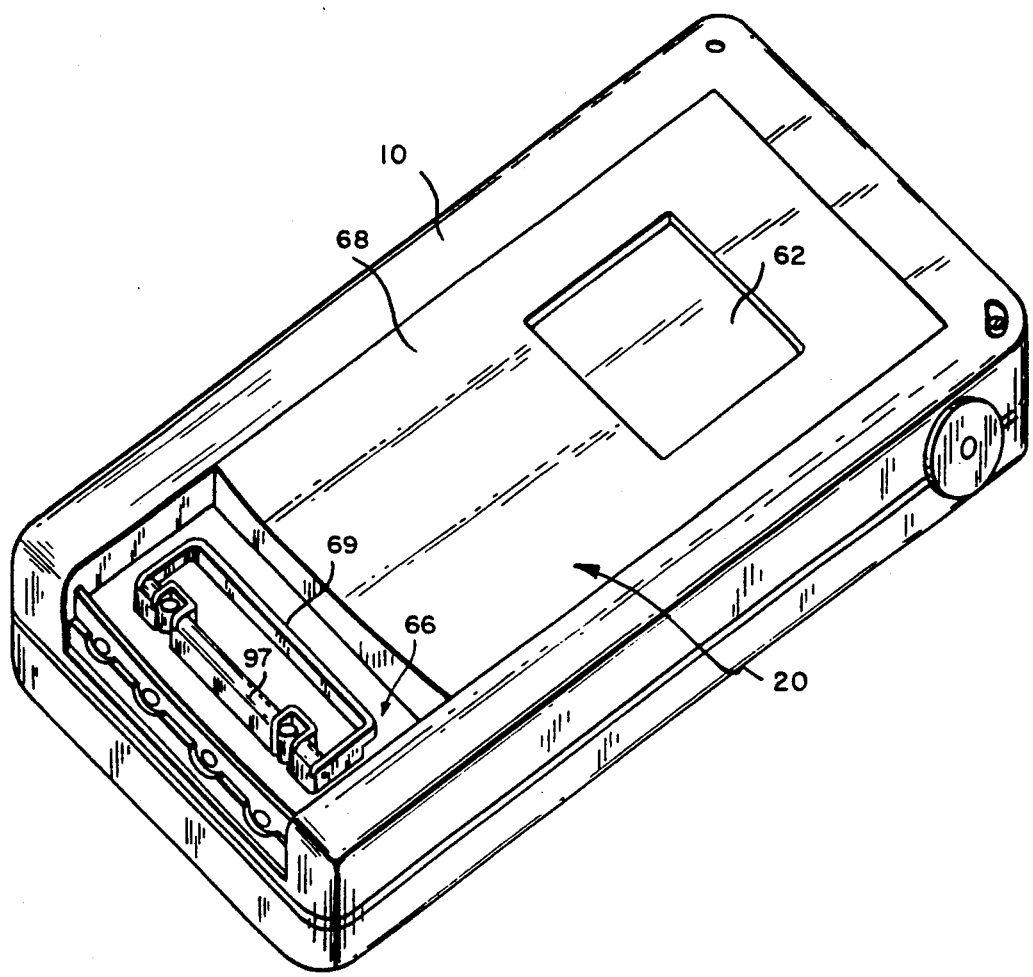
FIG. 8 is an isometric view of the underside of an infusion pump with a cartridge of the present invention inserted.
Figure 9:
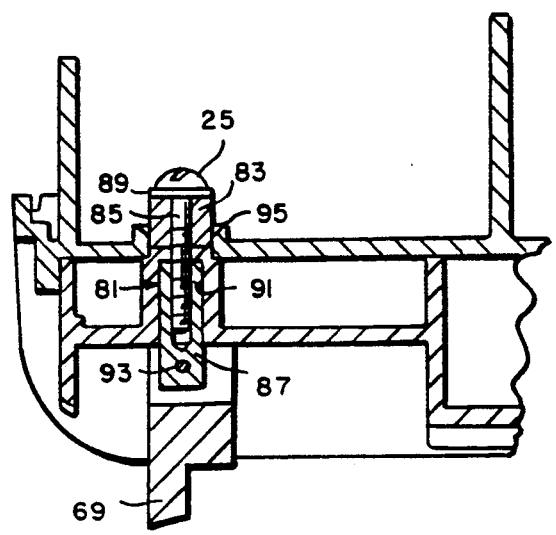
FIG. 9 is a partial cross-sectional view of the cartridge of the present invention inserted into an infusion pump with the clamp open.
Figure 10:
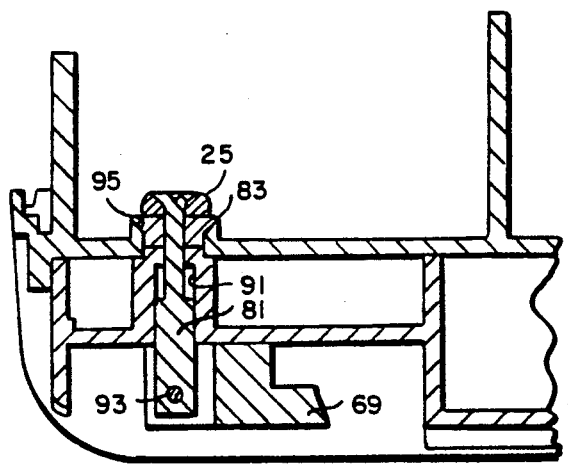
FIG. 10 is a partial cross-sectional view of the pump and cartridge of FIG. 8 with the clamp closed.

Referring now to FIGS. 8-10, the mechanics for holding the cartridge in place against the pump shall be described. A clamp is located in the pump interface portion of the cartridge. Since this is where the pump tubes are located, it is critical that this portion of the cartridge be repeatably and accurately positioned and held against the infusion pump. It is important that the pump interface portion 66 of the cartridge 20 be held in a fixed position against the pump, since if the position is off it is possible that one of the pump fingers would not fully close off a pump tube as required to provide precise infusion rates.

The clamp includes two clamping posts 81 each with a clamp head 25. The clamping posts and clamp head are made of stainless steel in the presently preferred embodiment. Surrounding each clamping post 81 beneath its clamp head 25 is a compressible elastomeric tube 83, made of silicone in the presently preferred embodiment. The clamping post 81 may be formed by a screw 85 and threaded shaft 87 as shown in FIG. 9. Alternatively, the clamping post 81 may be a single rod with a flaired top portion as shown in FIG. 10. The clamp head 25 in FIG. 9 is formed by a washer 89 and the head of the screw 85. The clamp head 25 is formed about the flaired top of the rod in FIG. 10. The clamping posts 81 are axially movable within mounting walls 91 in the pump interface portion of the cartridge.

At the end of each clamping post 81 extending through the bottom of the cartridge 20, is inserted an expansion pin 93. The expansion pins 93 act as an axle about which the clamp handle 69 can be rotated. The pins 93 engage a hole in the clamp handle which is positioned so as to be a short distance from one edge and a longer distance from a second edge. As shown in FIG. 9, when the handle 69 is protruding out from the cartridge, the expansion pin 93 is between the handle and the edge which is a short distance from the pin. Thus, the pin is held a short distance from the bottom side of the pump interface portion of the cartridge. When the clamp handle 69 is pushed against the cartridge, the expansion pin 93 is pulled on until the clamp handle 69 rests on its side. With the handle on its side against the cartridge the expansion pin 93 has been pulled into a second position in which it is a longer distance from the bottom side of the pump interface portion. In this second position, the clamp head 25 is pulled down against the silicone tube 83. The tube 83 is compressed axially and expands radially. The tube 83 expands filling a countersunk hole 95 in the infusion pump base.

When the clamp is in the locked position as shown in FIGS. 8 and 10, the expansion pins 93 pull the clamp handle 69 upwards and the clamp head downwards. This secures the pump interface portion a fixed distance from the infusion pump base. The clamping action is sufficiently strong so that any affects of the pump fingers are insignificant. Additional support may be provided by an inner bar 97 which is a part of the handle 69 stretching between the clamping posts. The handle 69 and inner bar 97 are made from Delron in accordance with the presently preferred embodiment. The handle with its inner bar 97 extends across all four of the pump tube locations. Thus, the pull of the clamp is directly applied underneath each of the pump tubes. In this manner, the clamp of the present invention advantageously rigidifies and supports the base under each of the pump tubes maintaining the base at an accurate distance from the pump fingers.

Figure 11:
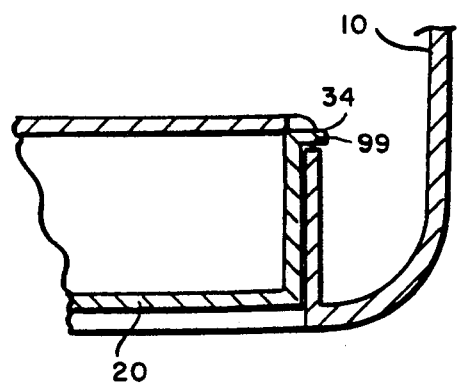
FIG. 11 is a cross-sectional view of the rear portion of the pump and cartridge of FIG. 8.

FIG. 11 shows the engagement of the rear portion of a cartridge 20 with the pump housing. In order to insert a cartridge 20 into an infusion pump, the rear edge is inserted first. Tabs 34 are inserted into mating holes 99 in the pump housing 10. Then the pump interface portion of the cartridge is swung up into place. The clamp heads 25 enter the pump housing 10 through the countersunk holes 95 when the cartridge 20 is properly positioned. When the cartridge is in place, the clamp handle 69 is pushed against the cartridge to secure the cartridge in place. The key operated latch 36 may also be secured against the cartridge to protect against unauthorized access to the drug solutions in the cartridge.

The pump tube mounts for insertion into a cartridge are shown in FIGS. 12-16. The front wall 84 of a pump tube mount can be seen in FIG. 12. The front wall 84 is shaped so as to mate with the openings 80 in the cartridge. Extending from the front wall 84 is an outlet 26 which is preferably a female luer connector. Two side walls 86 connect the front wall 84 to a rear wall 88. The rear wall 88 of the pump tube mount extends downward below the base 67 of the pump tube mount. At the lower end of the rear wall 88 is a pair of tabs 90 which engage the lower edge 78 of the ledge 75 in the cartridge 20. The dividing wall 64 in the cartridge 20 is discontinuous providing openings for each of the pump tube mounts. Also illustrated in FIG. 12 is a bag spike 92, which is inserted into a bag of fluid solution hanging from a pole to connect the pump with the fluid solution.

FIG. 13 shows how the pump tube mount is inserted into the cartridge. The rigid base 67 beneath the pump tube 22 does not extend all the way to the front wall or the rear wall. At the front wall, this provides a space into which the retaining stump 82 can be extended. Thus, the first step, is to position the front wall 84 up against the stump 82. The rear wall 88 is then lowered over the ledge 75 in the cartridge 20. As the rear wall 88 is lowered, the front wall 84 pivots into place within the opening 80. The rear wall 88 is lowered until the tabs 90 snap into the openings beneath the lower edge 78. The rear wall 88 is located so as to fit snugly against the ledge 75. Thus, when the tabs 90 have not yet been lowered into the openings beneath the edge 78, the tabs 90 are forcing the rear wall 88 away from its normal resting position. Once the tabs get beneath the lower edge 78, the rear wall 88 is free to resume its resting position and therefore springs back against the ledge to make a snapping noise. The snap can be heard and felt so as to reassure the user that the pump tube mount is correctly positioned. The engagement of the tabs and the lower edge 78 keeps the pump tube mount in its correct position. When in place, the rear wall 88 against the ledge 75 prevents the pump tube mount from moving forward. This, in combination with the retaining stump 82 and the opening 80 securely holds the pump tube mount in a known position in three dimensions.

Figure 14:
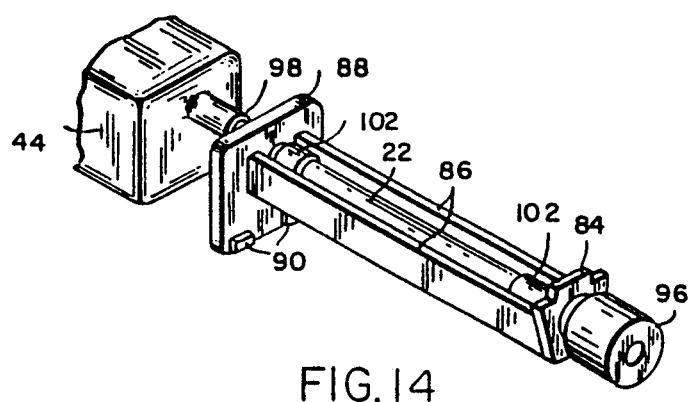
FIG. 14 is an isometric view of the pump tube mount attached to a fluid source pouch.

FIG. 14 illustrates a disposable pump tube mount. The tube mount, according to the presently preferred embodiment, is made of polycarbonate. The pump tube mount shown is attached to a flexible fluid source pouch 44. The fluid source pouch 44 may be adhesively bound to an inlet 94 extending from the rear wall 88 of the pump tube mount. A luer cap 96 may be screwed on to the luer connector 26 when the tube mount is not hooked up to an output line.

Figure 15:
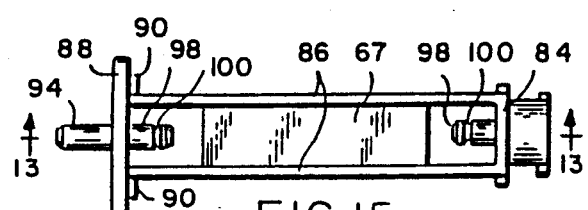
FIG. 15 is a plan view of the pump tube mount without the tube and its retaining rings.

In FIG. 15, the pump tube mount is shown without a tube 22. Extending inwards from the front wall and the rear wall 88 is a fitting 98. The fitting 98 has a cylindrical exterior portion which makes surface contact with the inner circumference of the tube 22. The surface contact provides a frictional force between the fitting 98 and the inner circumference of the tube 22. In certain applications, this frictional force may be sufficient to hold the tube on the fittings. The presently preferred material for the tube 22 is Dow Corning medical-grade silicone.

Further force to hold the pump tube on the fitting may be provided by a barb extending from the fitting to dig in and hold onto the tube. Alternatively, in accordance with the presently described embodiment, an indentation such as an annular groove 100 is made in the cylindrical fitting 98. If the tube 22 fits tightly enough over the fitting 98, the silicone will slightly extend into the groove 100. This will provide an edge against the fitting which will hold the tube in place. To ensure that the silicone is depressed into the groove 100, a collar 102 may be placed over the tube concentrically aligned with the groove 100. The engagement of the tube with the groove provides adequate resistance against the shear forces created by the pumping action. The collar 102 is preferably a rigid material which is sized to compress the silicone into the groove 100. The collar 102 may be made from a material such as PVC or stainless steel.

Figure 16:
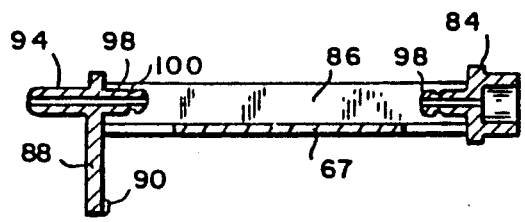
FIG. 16 is an elevational view of the pump tube mount of FIG. 15.

Referring now to FIG. 16, the rigid base 67 is shown. The base 67 is supported by the sidewalls 86 of the pump tube mount. As can be seen in FIG. 16, there is a space between the rigid base 67 and the front wall 84 into which the stump 82 can extend. In operation, the base 67 rests against the bottom of the pump interface portion of the cartridge and is securely held in position by the clamp which extends across the pump interface portion.

Figure 18A:
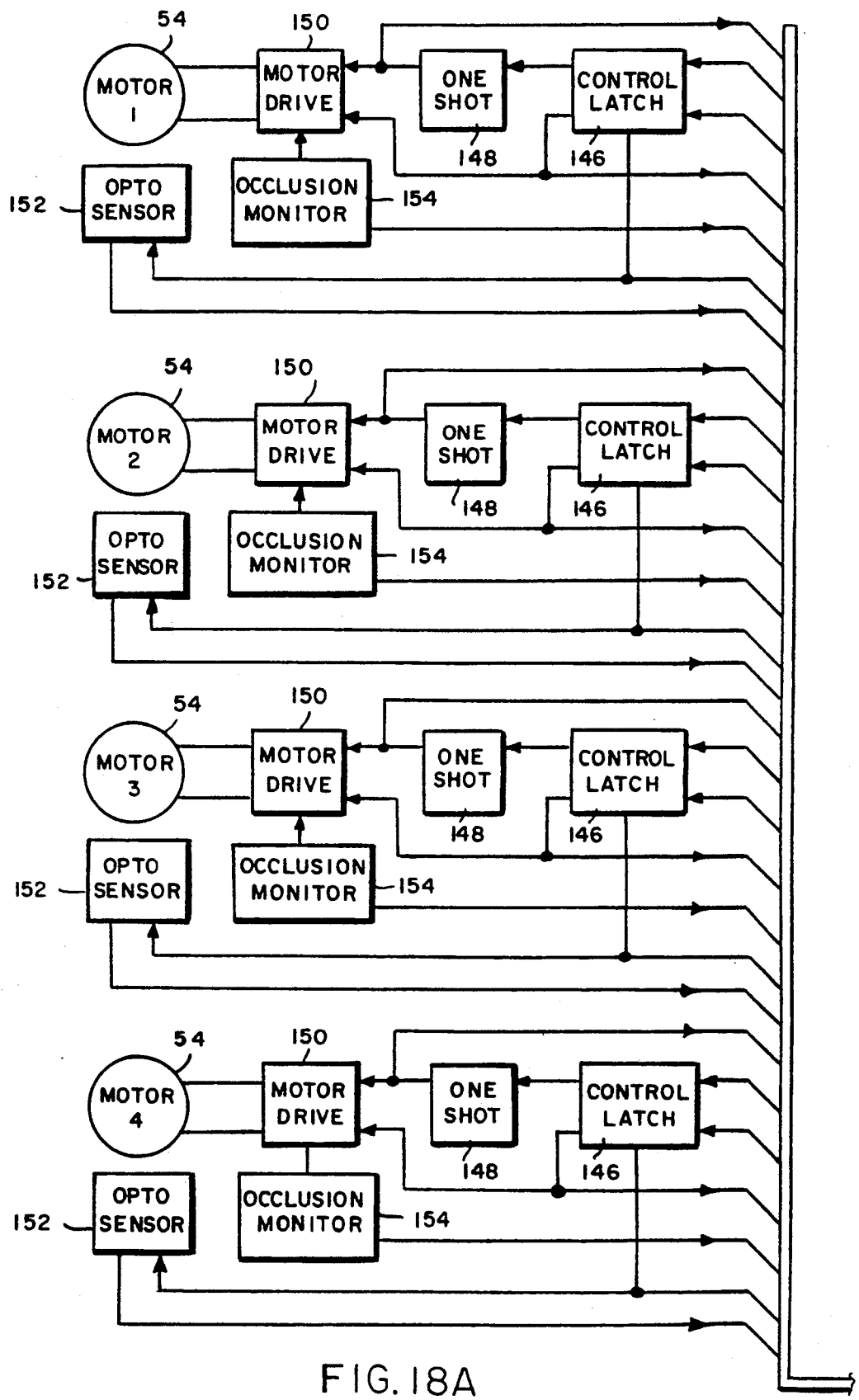
FIGS. 18A and 18B are a schematic of the circuitry for operating the pump motors.
Figure 18B:
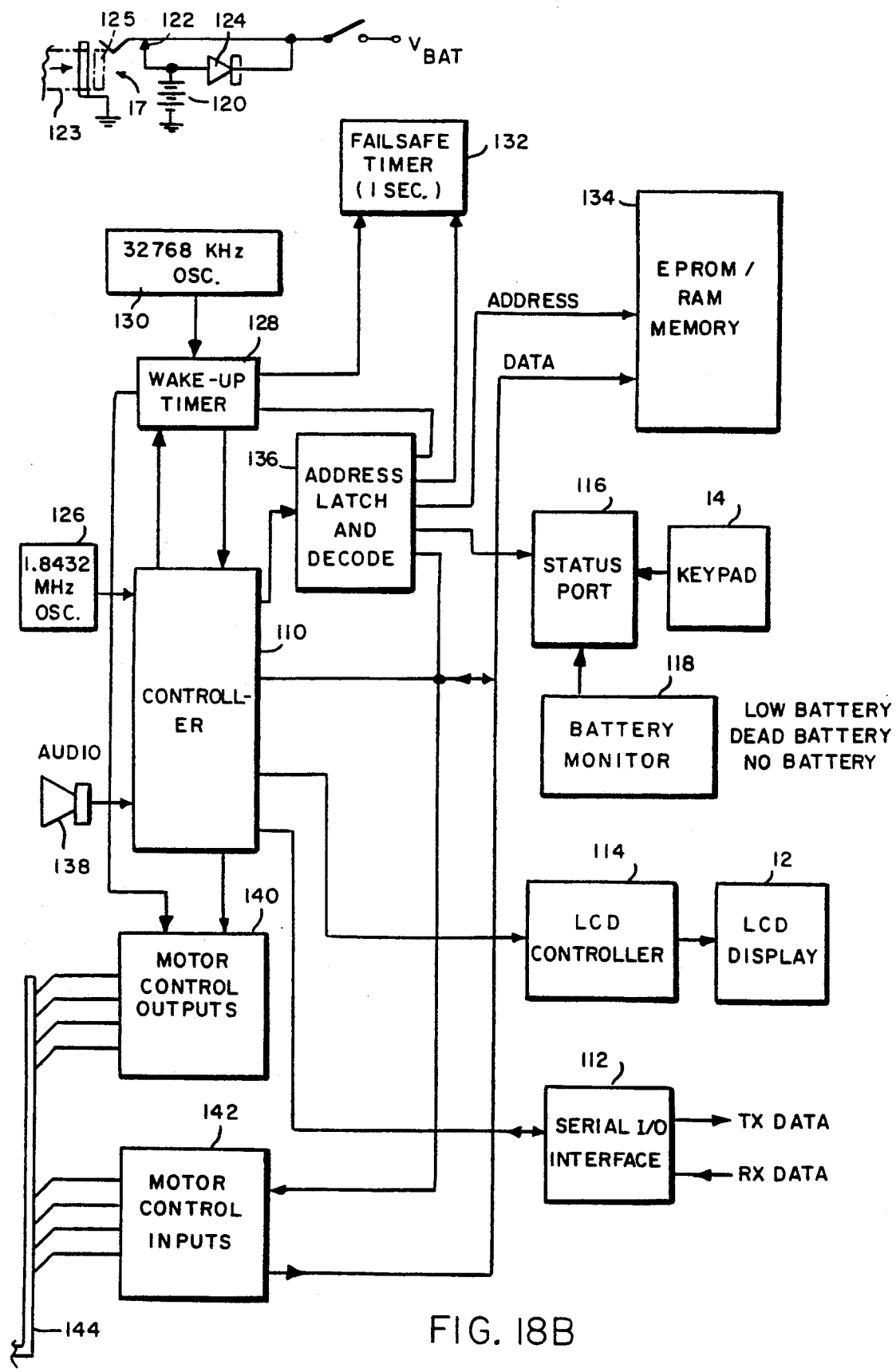
Figure 19:
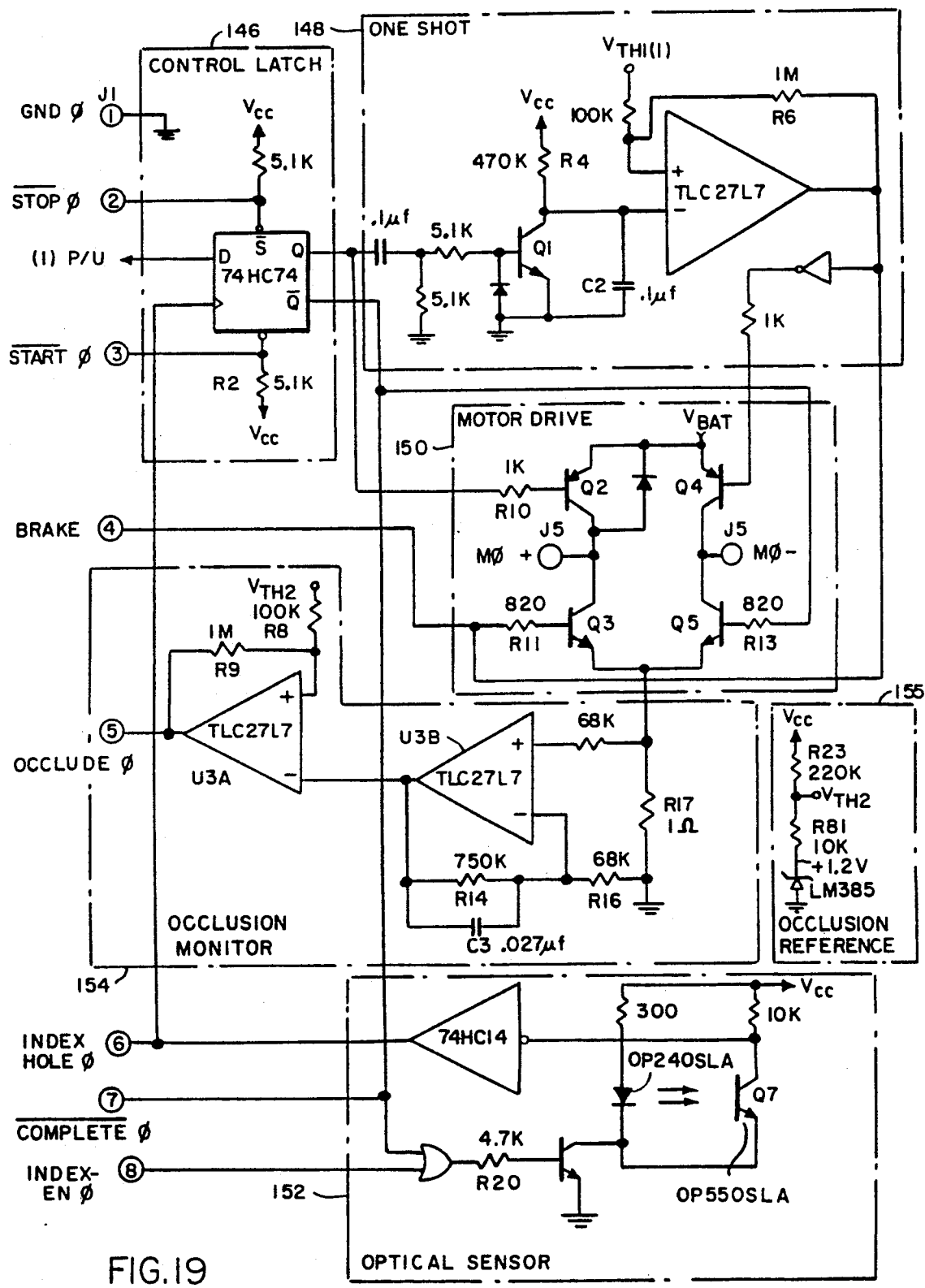
FIG. 19 is a schematic of the electronic circuitry devoted to a single pump motor.

The electronics for operating a direct current motor in the infusion pump of the present invention shall be described with reference to FIGS. 18A, 18B and 19. The program functions of the infusion pump are controlled by a microprocessor 110. The presently preferred microprocessor is an 80C31. A connection is provided between the microprocessor 110 and a serial I/0 interface 112. The serial interface provides for bi-directional communication between the programmable infusion pump and attached equipment. Applications for the serial I/0 interface include 1) the receipt of an infusion schedule from an external programmer, 2) external initiation of a self-test mode with transmission of the self-test status, 3) external initiation of diagnostic functions, and 4) externally triggered events such as a schedule stop or a special infuse sequence.

The microprocessor operates the liquid crystal display 12 through an LCD controller. The presently preferred LCD controller is a Philips PCF 2111.

A status port 116 interacts with the keypad 14 and battery monitor 118. The battery monitor 118 detects when the battery is either low, dead or not inserted.

The internal battery 120 may be used to supply power to the circuitry. A power jack 17 permits the pump to be run on external power rather than using the battery 120. The voltage provided by the battery or power jack is indicated as $V_{BAT}$. A schottky diode reduces $V_{BAT}$ about a quarter of a volt to get $\gamma cc$ which is used by most of the circuitry. When a plug 123 for providing power is fully inserted into the power jack 17 a switch 122 is forced open, breaking its contact. The power for the programming circuitry is then maintained by the external source. In order to avoid an undesirable break in the provision of power to the infusion pump when an external plug 123 is inserted into the power jack 17, a diode 124 is connected to the battery 120. When a battery is installed in the infusion pump, current can pass from the battery through the diode 124. When a power plug is inserted into the jack 17, a non-conducting end 125 of the plug may contact the switch and break the switch contact before electrical connection is made between the plug and the power line for the circuitry. When the switch is broken the battery continues to provide power through the diode 124 thereby avoiding a temporary loss of power. Once electrical contact is made between the external source and the power line, power is essentially provided by the external source and the diode 124 prevents the external power source from charging the non-rechargeable battery 120.

A timing signal is provided to the microprocessor 110 by a 1.8432 megaHertz oscillator 126.

A wake-up timer 128 divides the 32,768 Hz signal from an oscillator 130 so that a reset signal is delivered each sixteenth of a second from the wake-up timer to the microprocessor. The microprocesor is awakened each sixteenth of a second at which point it cycles through its control program. The microprocessor 110 manipulates and monitors counters to generate delays inserted between each motor startup to obtain a desired infusion rate. Each time the motor is started, it performs a complete pump cycle. Given a fixed volume of fluid delivered for a pump stroke, an infusion rate can be converted into a delay time between pump cycles. The delay time for the desired infusion rate for each pump is input into the pump control board through the programming jack 16. For example, a flow rate of 200 ml/hr converts to a delay of 14.4 sixteenths of a second for a stroke volume of 0.05 ml.

The processor keeps track of the whole and fractional cycles separately. If the cycle count is a whole number such as 14.0, then every fourteeen sixteenths of a second, (every 14 cycle periods), the motor will be started in a microprocessor program cycle. When a fractional cycle is required for a given rate, the fraction value is accumulated until it exceeds 1. Then, an additional cycle is added to the cycle count. For the case where the cycle time is 14.4 sixteenths, a first motor cycle will begin after 14 sixteenths. 4/10 is carried over. The next pump cycle will be started after the next 14 sixteenths. Again, 4/10 is added to the fraction accumulator, leaving 0.8 as the accumulated total. Fourteen clock periods later the motor will be started again. This time when the 4/10 is added to the accumulator, unity is exceeded with an additional fraction of 2/10. An additional cycle is added to the cycle count so that the next motor cycle will not begin until 15 clock periods later. The succeeding cycle will again have a cycle count of 14, until the fractional accumulator exceeds unity. Thus, for a pumping time of 14.4 sixteenths, the sequence will be 14, 14, 14, 15, 14, 14, 15. This will provide a sufficiently accurate infusion rate.

The fail safe timer makes sure that the motors are not operated if the microprocessor is not working properly. The microprocessor resets the fail safe timer each control program cycle, that is, each sixteenth of a second. Should the fail safe timer not be reset within a one second period, its output will stop the motors and the microprocessor will generate an error message.

Memory 134 is provided to work in conjunction with the microprocessor 110. The memory 134 includes EPROM for the permanent program storage and RAM for temporary storage of program instructions to control infusion and for general memory use. An address latch and decode circuit 136 is provided for interfacing the microprocessor 110 with the memory 134 and status port 116. The lower 8 bits of the microprocessor's address are multiplexed with the data bus, so the address must be latched synchronously with the address latch enable signal in order to distinguish it from data. The decoder portion of circuit 136 allows the microprocessor to enable any chosen one of the devices on the data bus.

The microprocessor 110 operates the motor control and an audio signaller 138. The audio signal may be generated in response to an alarm condition or to annunciate events such as a key press or serial link connect. Communication with the various motors in the infusion pump is handled through the output circuitry 140 and the input circuitry 142. The motor control input output circuitry communicates with the motors over a bus 144.

Each of the motors in the infusion pump is provided with circuitry for driving and controlling that motor. The circuit details of the presently preferred embodiment are shown in FIG. 19 for all of the motor driving control circuitry. The circuitry is the same for each one of the motors. A start signal from the microprocessor is received and latched in the control latch 146. This is passed to the one shot 148 where a signal is produced for operating a motor drive 150 in the forward direction. On the forward direction transistors Q2 nd Q5 shown in FIG. 19 are biased on. The motor drive may be an H bridge circuit so that it can produce a positive or negative signal to the motor.

The motor rotates in response to the signal from the motor drive 150 remaining on until the stop position is reached, as indicated by the optical sensor. The optical sensor 152 includes a light emitting diode 57 and a photodetector 59, which in the presently preferred embodiment is a phototransistor. When the motor shaft is in the stop position, the light from the LED is visible to the phototransistor and a signal is provided by the sensor indicating that the motor shaft is in its stop position. Once the motor shaft moves, the open sector in the position encoder rotates away from the optical sensing region and the solid portion of the position encoder blocks the light from the LED to the phototransistor 59. Once a complete cycle of the motor shaft has been made, an open sector of the position encoder reaches the optical sensing portion and the light from the LED becomes once again visible to the phototransistor. Thus, the optical sensor produces a signal indicating the stop position has been reached.

This stop signal resets the control latch 146, removing drive from Q2 and Q5. When the control latch 146 is reset, its output signal to the one shot 148 goes high and a signal opposite in polarity to the start signal is provided by the one shot to the motor drive 150. This opposite polarity signal causes the motor drive to operate in reverse for a time controlled by the RC time constant of R4 and C2. In the presently preferred embodiment, the reverse signal operates for about 36 milliseconds. The optical sensor sends a "complete" signal to the microprocessor so that it knows a revolution has been completed.

The microprocessor is operating a counter, waiting for the complete signal to be returned within sixteen control program cycles. If it isn't, an error message is generated. When a motor is idle, compliance is confirmed by reading the optical sensor signal to ascertain shaft position. Should the optical sensor provide a signal indicating the motor shaft has moved from its stop position, an off-line error is displayed by the processor. Should the optical sensor signal subsequently indicate the stop position has been reached, it is assumed that the motor is in a run-a-way condition and an alarm and error display is generated. Idle state monitoring is performed during the normal program control cycle and so occurs at the 16 Hz rate.

An occlusion monitor 154 is also provided. If the motor is having difficulty turning because of an occlusion in the catheter line or some other blockage, a signal will be fed from the motor drive 150 to the occlusion monitor 154. Referring to FIG. 19, this will be in the form of an increase in the motor current which flows through a 1 ohm resistor, R17. The voltage across R17 is sensed at a time when the pump plunger 48 is maximally depressed, since the motor current is proportional to load, occlusion can be sensed by comparing the voltage across R17 to a level consistent with normal operation. Reference voltage VTH2 in the occlusion monitor 154 represents the normal level.

VTH2 is provided by the occlusion reference 155. Rather than provide a fixed VTH2, the reference circuit 155 makes VTH2 a function of the battery voltage. In this manner, occlusion sensing is not sensitive to changing battery voltage. VTH2 is taken from a voltage divider formed by resistors R23 and R81. The voltage across R17 is amplified and filtered by amplifier U3B. The gain of U3B can be set by the value of R14 to be consistent with the value of VTH2, thereby causing comparator U3A to change state at the proper level of occlusion. Comparator U3A provides an "occlude" output when the output of U2B exceeds the normal established by VTH2. This will cause a signal to be sent over the bus 144 to the microprocessor. On detection of the occlusion signal, the microprocessor will send a stop signal to the motor, suspend the current infusion schedule and display the error condition on the infuser display. Since an increase in current across R17 will be caused by starting or stopping the motor, the microprocessor will not check the occlusion signal during those time frames. The microprocessor is programmed to check the occlusion signal only when the motor is at the stage where it is pushing down on the pump plunger 48.

As demonstrated by the above description, it is possible with the present invention to use a direct current motor in conjunction with the position encoder so as to achieve accurate infusion rates. Since one complete cycle of the motor can be repeated with precision and since the volume of fluid pumped during a complete cycle is accurately determinable, the volume per unit time can be precisely controlled by the microprocessor controlled infusion pump of the present invention by regulating the number of pump cycles per unit time.

Of course, it should be understood that various changes and modifications to the preferred embodiment described above will be apparent to those skilled in the art. For example, a combination of dynamic braking and reverse pulsing could be used to stop the motor. Also, the brake pulse width and, therefore, the energy expended could be modified by use of other sensing positions on the motor output shaft. Hall effect sensors and small magnets could be used to sense shaft position. These and other changes can be made without departing from the spirit and scope of the invention and without diminishing its attendant advantages. It is therefore intended that such changes and modifications be covered by the following claims.

We claim:
1. An infusion pump system comprising:
   a fluid source cartridge including a pump interface portion containing a plurality of linear fluid conduits each being connected to an output port and a fluid source portion from which fluid is provided to said plurality of fluid conduits;
   a pump housing having a plurality of linear peristaltic pumps each having a set of pump fingers, the sets of pump fingers being arranged on a common base; and
   means for receiving said fluid source cartridge onto said housing adjacent the common base such that each of said linear fluid conduits aligns with one of said linear peristaltic pumps so that for each fluid conduit, fluid is pumped by one of said linear peristaltic pumps.

2. The infusion pump system of claim 1 wherein said output ports communicate with a multilumen output tube which connects to a multilumen connector means.

3. The infusion pump system of claim 1 wherein said output ports communicate with a manifold which feeds all fluids into a single output lumen.

4. The infusion pump system of claim 1 further comprising a programmable controller in said pump housing for individually controlling each of said peristaltic pumps thereby permitting sequential operation of the pumps at individually selected pumping rates.

5. The infusion pump system of claim 1 further comprising a clamp in the pump interface portion of said cartridge for securing said cartridge to said pump housing.

6. The infusion pump system of claim 5 wherein said clamp comprises a pair of clamp posts, each clamp post having a clamp head for insertion into said pump housing and means for changing said clamp posts between an open and a closed position.

7. The infusion pump system of claim 1 further comprising:
a plurality of clamp posts extending from the pump interface portion of said cartridge, each post carrying an expandable member for insertion into said pump housing; and
means for pulling on said clamp posts to expand said expandable members and to secure said cartridge to said pump housing.

8. The infusion pump system of claim 7 further comprising a support extending beneath the pump interface portion and connected to said clamp posts such that when said clamp posts are pulled to secure said cartridge, said support helps rigidify the pump interface portion a fixed distance from said pump.

9. The infusion pump system of claim 1 wherein each of said linear peristaltic pumps is operated by a direct current motor which rotates a motor shaft.

10. The infusion pump system of claim 9 further comprising along with each motor shaft, a position encoder rotatable in conjunction with its respective shaft for identifying a repeatable stop position for said shaft.

11. The infusion pump system of claim 9 wherein each of said direct current motors is selectively operable in a forward or reverse direction, the reverse direction being operable to quickly stop said motor.

12. The infusion pump system of claim 1 further comprising within said pump housing:
a power supply line coupled to a battery;
a diode coupled between said battery and said power supply line; and
a receptacle for receiving a power jack to switch said power line into connection with said power jack instead of said battery, said diode permitting power to be provided by said battery until electrical contact is made between said power jack and said power supply line and said diode preventing said battery from being charged by said power supply line.

13. An infusion pump comprising:
a motor operable to rotate a motor shaft;
means for driving said motor;
a pump mechanism actuated by said motor shaft;
a fluid supply line situated relative to said pump mechanism so as to be acted on by said pump mechanism such that when said motor shaft is rotating, fluid is moved through said supply line;
processor means for initiating said driving means at selected intervals defined by a whole number of clock cycles to achieve a desired infusion rate which corresponds to intervals equal to the whole number and a calculated fracitonal value of clock cycles; and
a memory location for storing a number representative of the fraction of a clock cycle and for accumulating the calculated fractional value at each pump cycle, so that when the accumulated sum reaches at least 1.0, an additional clock cycle is temporarily added to the whole number of clock cycles in the selected interval.

14. The infusion pump of claim 13 further comprising a position encoder rotatable in conjunction with said motor shaft for identifying a repeatable stop position for said shaft.

15. The infusion pump of claim 14 further comprising optical means for reading said position encoder and for sending a stop signal to said driving means when said motor shaft has completed a pump cycle.

16. The infusion pump of claim 15 wherein said optical means monitors said position encoder when said driving means is not being operated to ensure that said motor shaft has remained in the stop position.

17. The infusion pump of claim 13 wherein said pump mechanism comprises a plurality of finger members forming a linear peristaltic pump.

18. The infusion pump of claim 13 wherein said driving means is operable to selectively drive said motor in a forward or reverse direction, the reverse direction being usable to quickly stop said motor.

19. The infusion pump of claim 13 further comprising a battery for supplying power to said motor and a circuit for comparing current required by said motor with a reference which is a function of the voltage supplied by said battery for detecting an occlusion in said fluid supply line.

20. The infusion pump of claim 13 further comprising a power supply line coupled to a battery; a diode coupled between said battery and said power supply line; and a receptacle for receiving a power jack to switch said power line into connection with said power jack instead of said battery, said diode permitting power to be provided by said battery until electrical contact is made between said power jack and said power supply line and said diode preventing said battery from being charged by said power supply line.

21. The infusion pump of claim 13 wherein said motor comprises a direct current motor.

22. A multiple fluid infusion pump comprising:
a plurality of direct current motors each operable to rotate a motor shaft;
means for driving each of said motors;
a plurality of pump mechanisms arranged on a common base, each including a set of pump fingers which reciprocate through the base upon actuation by one of said motor shafts; and
a plurality of fluid supply lines, each situated relative to one of said pump mechanisms so as to be acted on by its respective pump mechanism such that when the motor associated with said pump mechanism is rotating, fluid is moved through said supply line.

23. The multiple fluid infusion pump of claim 22 wherein said pump is an ambulatory pump.

24. The multiple fluid infusion pump of claim 22 wherein each of said pump mechanisms comprises a plurality of finger members forming a linear peristaltic pump.

25. The infusion pump of claim 22 wherein each of said driving means is operable to selectively drive its respective motor in a forward or reverse direction, the reverse direction being usable to quickly stop said motor.

26. The infusion pump of claim 22 further comprising a power supply line coupled to a battery; a diode coupled between said battery and said power supply line; and a receptacle for receiving a power jack to switch said power line into connection with said power jack instead of said battery, said diode permitting power to be provided by said battery until electrical contact is made between said power jack and said power supply line and said diode preventing said battery from being charged by said power supply line.

27. An infusion pump comprising:
a housing having a platform;
a plurality of linear peristaltic infusion pumps, each pump having a plurality of pump fingers, said pumps being arranged in said housing so that said pump fingers reciprocate in and out through said platform; and
means for receiving a plurality of linear fluid conduits such that each of said linear fluid conduits aligns with the pump fingers of one of said linear peristaltic pumps so that for each fluid conduit, fluid is pumped by one of said linear peristaltic pumps.

28. The infusion pump of claim 27 further comprising a programmable controller in said housing for individually controlling each of said peristaltic pumps thereby permitting sequential operation of the pumps at individually selected pumping rates.

29. The infusion pump of claim 27 further comprising a manifold in communication with each of said fluid conduits for feeding all fluids into a single output lumen.

30. The infusion pump of claim 27 wherein each of said linear peristaltic pumps includes a direct current motor for rotating a shaft which is used to cause said pump fingers to reciprocate.

31. The infusion pump of claim 27 wherein each plurality of pump fingers is arranged parallel to one another in said platform.

32. The infusion pump of claim 27 further comprising:
a power supply line extending within said housing for coupling to a battery;
a diode coupled between said battery and said power supply line; and
a receptacle for receiving a power jack to switch said power line into connection with said power jack instead of said battery, said diode permitting power to be provided by said battery until electrical contact is made between said power jack and said power supply and said diode preventing said battery from being charged by said power supply line.

33. The infusion pump of claim 27 further comprising a plurality of position encoders each rotatable in conjunction with one of said motor shafts for identifying a repeatable stop position for said shaft and a plurality of optical means each for reading said position encoder and for sending a stop signal to said driving means when said motor shaft has completed a pump cycle.

* * * * *